(12) United States Patent
Baum et al.

(10) Patent No.: US 7,429,392 B2
(45) Date of Patent: Sep. 30, 2008

(54) COATING MATERIAL WITH BIOCIDE MICROCAPSULES

(75) Inventors: Rüdiger Baum, Waghäusel (DE); Dagmar Antoni-Zimmermann, Speyer (DE); Thomas Wunder, Neustadt (DE); Hans-Jürgen Schmidt, Speyer (DE)

(73) Assignee: THOR GmbH, Speyer (DE)

( * ) Notice: Subject to any disclaimer, the term of this patent is extended or adjusted under 35 U.S.C. 154(b) by 639 days.

(21) Appl. No.: 10/489,842

(22) PCT Filed: Jun. 19, 2002

(86) PCT No.: PCT/EP02/06806

§ 371 (c)(1),
(2), (4) Date: Mar. 15, 2004

(87) PCT Pub. No.: WO04/000953

PCT Pub. Date: Dec. 31, 2003

(65) Prior Publication Data

US 2004/0234603 A1    Nov. 25, 2004

(51) Int. Cl.
*A01N 25/08* (2006.01)
*A01N 59/06* (2006.01)

(52) U.S. Cl. .................. 424/405; 424/409; 424/682

(58) Field of Classification Search .................. 424/405, 424/406, 407, 409, 421, 682, 724; 514/372
See application file for complete search history.

(56) References Cited

U.S. PATENT DOCUMENTS

| 5,084,506 A * | 1/1992 | Faler et al. .................. 524/597 |
| 6,267,590 B1 * | 7/2001 | Barry et al. .................... 433/8 |
| 6,280,759 B1 | 8/2001 | Price et al. |
| 6,413,011 B1 * | 7/2002 | Sobczak et al. ............... 404/72 |
| 6,905,698 B1 * | 6/2005 | Aldcroft et al. ............. 424/405 |

FOREIGN PATENT DOCUMENTS

| JP | 11-323185 | 11/1999 |
| JP | 2002-053412017179 | 2/2002 |
| WO | WO 99/56542 | 11/1999 |
| WO | WO 01/24631 A1 | 1/2001 |
| WO | WO03/089561 A2 | 10/2003 |

OTHER PUBLICATIONS

Chemical Abstracts + Indexes. American Chemical Society. Columbus, Ohio, US, vol. 111 No. 22. Nov. 27, 1989, p. 373.
Chistopher A. Finch: "Microencapsulation" Ullman's Encyclopedia of Industrial Chemistry, Online! Jun. 15, 2000 XP-002231333.

* cited by examiner

*Primary Examiner*—Sharon E. Kennedy
(74) *Attorney, Agent, or Firm*—James V. Costigan; Hedman & Costigan, P.C.

(57) ABSTRACT

The invention relates to a coating material for protection against microorganism invasion on surfaces which are exposed to the effects of damp or water. The coating material has either a pH-value of at least 11.0 or is provide with a base material for the coating whereby the pH-value is at least 11. The coating material is characterized in that it contains a biocide which bonds to solid particles in a carrier material and is released in a delayed manner therefrom.

9 Claims, No Drawings

COATING MATERIAL WITH BIOCIDE MICROCAPSULES

The invention relates to a coating material for protection against microorganism infestation on surfaces which are exposed to the effects of damp or water, said coating material either itself having a pH of at least 11.0 or being intended for the coating of a substrate material whose pH is at least 11.0. The invention pertains in particular to plasters and paints which are to be protected with biocides against attack by microorganisms.

It has long been known that fungicidal and/or algicidal biocides are added to plasters and paints in order to preserve films thereof. The purpose of this is to prevent unwanted infestation of the films by microorganisms, e.g., fungi, such as molds and yeasts, and also by bacteria, algae, and cyanobacteria (see D. Antoni-Zimmermann, P. Hahn, "Wässrige Siliconharz-Beschichtungssysteme für Fassaden" [Aqueous silicone resin coating systems for facades], expert. verlag, volume 522, pages 379 to 406). Such microorganism infestation occurs, for example, in the case of building facades provided with corresponding plasters and paints. These facades discolor as a result of the growth of the microorganisms and therefore require a new surface treatment after just a relatively short time, depending on the weathering situation.

On the one hand this affects those masonry coatings whose pH is in a range that allows the microorganisms to grow. The coating systems in question here are normally synthetic-resin-bound coating systems.

On the other hand, however, it also applies to silicate-bound plasters or paints. It is true that the pH of such systems is often in such a high range, owing to the high fraction of alkaline compounds, that initially there is no infestation by the microorganisms. Dispersion-based silicate coatings have a pH of from 11 to 11.5 when applied to a masonry construction. Pure silicate coatings or cementitious systems frequently have an even higher pH.

However, these high pH values subside over the course of time. This occurs on the one hand owing to neutralization of alkaline constituents of the coating material by atmospheric carbon dioxide. On the other hand, however, there are apparently further causes of microorganism infestation even in the case of strongly alkaline coatings. In recent times more and more cases have arisen in which, despite an alkaline coating on building facades, overgrowth by algae or fungi, for example, occurs after just a relatively short time. One possible cause of this might lie in the use of increasingly thicker or increasingly higher-quality heat insulation materials which are fitted to the building facades beneath the coatings, partly as a consequence of new heat insulation provisions. The improved insulation reduces heat exchange between the interior of the building and the outer surface of the coating. This promotes condensation and retards the drying of the exterior coating (see J. P. Blaich, "Die Gebäudehülle" [The building shell], Fraunhofer IRB Verlag, pages 46 to 58, especially pages 48 to 50, section 3, "Tauwasserniederschlag" [Condensation]).

The better the thermal insulation of a building facade the more quickly, and the greater the period of time, for which the temperature will fall below the dew point there. The consequence of this is the promotion of leaching of alkaline constituents from the surface of the facade, whose pH consequently falls more rapidly into a relatively lower range, in which the plaster or the paint again allows microorganisms to grow. At the same time, owing to the relatively long moisture cycles, there is also an increase in the extent of infestation.

EP 1108824 A1 discloses a building material comprising microcapsules containing hinokitiol as active substance. Said active substance is intended to emerge from the microcapsules over a prolonged period of time and to spread within the building material in order thus to eliminate, for example, microbes and bacteria. Hinokitiol is inadequate as a biocide for specifically suppressing the growth of algae and fungi on building facades to a sufficient extent.

EP 0758633 B1 describes porous granules which are loaded with chemical substances in such a way as to act as a store for these substances and to release them slowly. An example of one such chemical substance is a biocide. The material of the granules can, for example, be a porous ceramic material.

DE 4324315 A1 reports on a final-coat plaster composition which can where appropriate include an added biocide. In no way, however, is this biocide protected from decomposition.

It is an object of the invention to specify a coating material, in particular a plaster or paint, for protection against microorganism infestation on surfaces exposed to the effects of damp or water. The aim here is that microorganism infestation should be retarded or prevented even when on the surface that is to be protected an initially high pH falls in the course of time.

This object is achieved by the invention by means of a coating material of the type specified at the outset which is characterized in that the coating material comprises a biocide which is bound in a carrier material composed of particulate solids and is released retardedly therefrom.

In accordance with a first embodiment the coating material of the invention has a pH of at least 11. This has the advantage that, following application to the surface that is to be protected, the coating material, by virtue of its alkaline-range pH, initially halts the growth of microorganisms, particularly of algae and fungi. A further advantage is that when over the course of time, as a result of the effect of atmospheric carbon dioxide and also of condensation and rainwater, the alkaline constituents of the coating material become more and more neutralized and are leached from the coating material, and the pH of the material reduced as a result would allow microorganisms to grow again, the carrier material used in accordance with the invention gradually releases the biocide it contains and so prevents further growth of the microorganisms. All in all, therefore, the coating material maintains a flawless appearance of the surface that is to be protected, and does so for a relatively long time. Absent the invention, a silicate-bound coating material, which by its nature has a relatively high pH, could not be provided from the start with a biocide mixed in in the usual way, since the biocide would be decomposed in the strongly alkaline environment. Additionally, absent the invention, such a coating material would also lose its biocidal activity within a relatively short time, through leaching of the alkaline constituents, and would again allow algal or fungal growth.

In accordance with a second embodiment of the invention the coating material may also have a pH of well below 11.0, such as a pH of 8.5. In that case it is envisaged for application to a strongly alkaline substrate, e.g., to concrete or to the cement-bound reinforcing plaster of an exterior insulation and finishing system. In this case, alkaline compounds gradually penetrate from the substrate material into the coating containing the biocide, and as a result of the increase in pH would normally decompose an unprotected biocide therein. This would be the case, for example, if the coating were applied to the strongly alkaline substrate before its pH had fallen, as a result of atmospheric carbon dioxide, to a level at which the biocide remains stable. In the case of isothiazolinones as active biocidal substances, for example, the pH would have to fall to about 4 to 9.

If in such a case, namely that of a strongly alkaline substrate, the biocide were to be added to the coating in conventional manner, i.e., without the particulate-solids carrier material used in accordance with the invention, as is the case, for example, with known synthetic-resin-bound plasters and paints, the biocidal effect achieved would be inadequate, or there would be none at all. The reason is that the strongly alkaline constituents penetrating the coating from the substrate decompose the biocide and/or convert it into a soluble form. The substances produced in this process no longer have a biocidal effect and/or are rapidly leached. Since only a few biocides with high stability in the strongly alkaline range are known, and in this range, therefore, the activity spectrum with respect to microorganisms is greatly restricted, the invention provides a substantial improvement in this respect.

The coating material of the invention is preferably a silicate-bound or mineral plaster having a pH of at least 11 or a synthetic-resin-bound or silicone-resin-bound plaster having a pH of below 11.

In addition it is preferable for the coating material to be a silicate-bound paint having a pH of at least 11 or a synthetic-resin-bound or silicone-resin-bound paint having a pH of below 11.

In accordance with the microorganisms which occur primarily in the environment of plasters and paints, it is preferred in accordance with the invention for the biocide to be a fungicide, an algaecide or a combination of the two. It is also possible here to use more than two biocides simultaneously.

Fungicides preferred in the context of the invention are isothiazolinones, carbamates, pyrithiones, aldehydes, ketones, quinones, amines, amidines, guanidines, hydrazo and azo compounds, aromatic carbonitriles, carboxylic esters, carboxamides and carboximides, benzimidazoles, quinoxalines, imidazoles, triazoles, pyrimidines, triazines, halogenated and nitrated alcohols and phenols, perhaloalkyl mercaptan derivatives, phosphoric and phosphonic esters, tetrahydro-1,3,5-thiadiazinethiones, thiocyanates and isothiocyanates, thiophenes, antibiotics, and active plant substances. Specific examples of fungicides highly suitable in accordance with the invention are methyl 1H-benzimidazol-2-ylcarbamate (carbendazim), 2-pyridinethiol 1-oxide zinc (zinc pyri-thione), 2-n-octylisothiazolin-3-one (OIT), 4,5-dichloro-octylisothiazolin-3-one (DCOIT), and 3-iodo-2-propynyl N-butylcarbamate (IPBC).

Algicides preferred in the context of the invention are triazines, N,N-dimethylureas, and uracils. Specific examples of algicides highly suitable in accordance with the invention are $N^2$-t-butyl-$N^4$-ethyl-6-methylthio-1,3,5-triazine-2,4-diyldiamine (terbutryn), 2-chloro-4,6-bis(isopropylamino)-s-triazine, 2-t-butylamino-4-ethylamino-6-methoxy-s-triazine, 2-methylthio-4-butylamino-6-cyclopropylamino-s-triazine, 4-butylamino-2-chloro-6-ethylamino-s-triazine, 3-(4-isopropylphenyl)-1,1-dimethylurea, N'-(3,4-dichlorophenyl)-N,N-dimethylurea, and 3-t-butyl-5-chloro-6-methyluracil.

The particulate solids of the carrier material are preferably granular particles with cavities.

It is advantageous for these granular particles to be in the form of microcapsules. Within these microcapsules the biocides are enclosed in a finely dispersed, liquid or solid phase. Suitable wall materials for the microcapsules include a very wide variety of substances: natural, semisynthetic, and synthetic materials.

Natural materials preferred in the context of the invention for the microcapsule walls are gum arabic, agar, agarose, maltodextrin, sodium alginate, calcium alginate, dextran, fats, fatty acids, cetyl alcohol, milk solids, molasses, gelatine, gluten, albumin, shellac, starches, caseinates, stearins, sucrose, and also waxes, such as beeswax, carnauba wax, and spermaceti wax.

Preferred semisynthetic materials for the microcapsule walls are cellulose acetate, cellulose acetate butyrate, cellulose acetate phthalate, cellulose nitrate, ethylcellulose, hydroxypropylcellulose, hydroxypropylmethyl-cellulose, hydroxypropylmethylcellulose phthalate, methyl-cellulose, sodium carboxymethylcellulose, hydrogenated tallow, myristyl alcohol, glyceryl mono- or dipalmitate, hydrogenated castor oil, glyceryl mono- or tristearates, and 12-hydroxystearyl alcohol.

Preferred synthetic materials for the microcapsule walls are formaldehyde-melamine resins, acrylic polymers and copolymers, such as polyacrylamide, polyalkyl cyanoacrylate, and poly(ethylene-vinyl acetate), aluminum monostearate, carboxyvinyl polymers, polyamides, poly(methyl vinyl ether-maleic anhydride), poly(adipyl-L-lysine), polycarbonates, polyterephthalamide, poly(vinyl acetate phthalate), poly(terephthaloyl-L-lysine), polyaryl sulfones, poly(methyl methacrylate), poly($\epsilon$-caprolactone), polyvinylpyrrolidone, polydimethylsiloxane, polyoxyethylenes, polyesters, polyglycolic acid, polylactic acid and copolymers thereof, polyglutamic acid, polylysine, polystyrene, poly(styrene-acrylonitrile), polyimides, and polyvinyl alcohol.

Particularly preferred microcapsule wall materials are formaldehyde-melamine resins. The microcapsule walls may also be composed of two or more of the aforementioned materials.

There are numerous known methods of preparing the microcapsules used as carrier material in the context of the invention (see, for example, C. A. Finch, R. Bodmeier, Microencapsulation, Ullmann's Encyclopedia of Industrial Chemistry, 6th Edition 2001, Electronic Release). The appropriate method in each case can be selected in accordance with the desired biocide and the microcapsule wall material to be employed.

It is also advantageous if the granular particles with cavities that are used are particles whose cavities are, for example, pores formed by foaming of the material, as in the case of a foamed ceramic material or in the case of expanded clay, or if the cavities are structural cavities, such as are present in zeolites.

Suitable granular particles in the form of a foamed ceramic material, and a variety of methods of preparing them, are known from EP 0758633 B1, for example. Further carrier materials, such as zeolites, are described in DE 4337844 A1.

The aforementioned particulate solids of the carrier material, e.g., as microcapsules, foamed ceramic material, zeolite, and the like, preferably have a size in the range from 30 to 40 µm.

In addition to the above-mentioned biocides and the materials for the microcapsule walls or for the porous granules, the coating material of the invention may include any substances which are commonly known and conventional in dependence on the intended use of the material. This includes, on the one hand, the corresponding binders and film formers, such as polyacrylates, polystyrene acrylates or silicone resins, and, on the other hand, the known auxiliaries, such as pigments, fillers, solvents, thickeners, defoamers, plasticizers, dispersants, emulsifiers, and agents for adjusting the pH of the coating material.

The examples illustrate the invention.

Preparation Examples 1 to 3 illustrate the preparation of microcapsules in which an active biocidal substance is enclosed.

Preparation Example 4 illustrates the preparation of a silicate-bound exterior plaster, Preparation Example 5 that of a synthetic-resin-bound float plaster.

Inventive Examples 1 to 4 and Comparative Examples 1 to 4 elucidate the superior stability of the plasters of the invention with respect to leaching of the biocide they contain.

Inventive Examples 5 and 6 and Comparative Examples 5 to 7 elucidate the growth of fungi on different plaster surfaces and the advantage achieved by the invention.

PREPARATION EXAMPLE 1

The substances indicated below were used to prepare microcapsules enclosing zinc pyrithione (2-pyridinethiol 1-oxide zinc) as active biocidal substance.

| Substances used | Amounts, g |
|---|---|
| Water | 389.6 |
| Polyacrylate (Coatex BR 3, Dimed) | 1.5 |
| Gum arabic | 0.6 |
| Silicone defoamer (Aspumit AP, Thor GmbH) | 0.3 |
| Zinc pyrithione powder | 60.0 |
| Concentrated hydrochloric acid | 4.0 |
| Formaldehyde-melamine resin (Quecodur DMQ, Thor GmbH) | 144.0 |
| | 600.0 |

For the preparation of the microcapsules the water was introduced first. Polyacrylate, gum arabic, silicone defoamer and the zinc pyrithione were stirred into the water. The resultant mixture was adjusted with hydrochloric acid to a pH of 3 and then heated to a temperature of 70° C. Subsequently the formaldehyde-melamine resin was added dropwise over 1 h. The mixture was subsequently stirred at the same temperature for a further 2 h.

The mixture obtained comprised the desired microcapsules and was used unchanged in preparing the microcapsule plaster.

PREPARATION EXAMPLE 2

The substances indicated below were used to prepare microcapsules enclosing DCOIT (4,5-dichloro-2-octylisothiazolin-3-one) as active biocidal substance.

| Substances used | Amounts, g |
|---|---|
| Water | 389.6 |
| Polyacrylate (Coatex BR 3, Dimed) | 1.5 |
| Gum arabic | 0.6 |
| Silicone defoamer (Aspumit AP, Thor GmbH) | 0.3 |
| DCOIT, 98% form | 60.0 |
| Concentrated hydrochloric acid | 4.0 |
| Formaldehyde-melamine resin (Quecodur DMQ, Thor GmbH) | 144.0 |
| | 600.0 |

For the preparation of the microcapsules the water was introduced first. Polyacrylate, gum arabic, silicone defoamer and the zinc pyrithione were stirred into the water. The resultant mixture was adjusted with hydrochloric acid to a pH of 3 and then heated to a temperature of 70° C. Subsequently the formaldehyde-melamine resin was added dropwise over 1 h. The mixture was subsequently stirred at the same temperature for a further 2 h.

The mixture obtained comprised the desired microcapsules and was used unchanged in preparing the microcapsule plaster.

PREPARATION EXAMPLE 3

The substances indicated below were used to prepare microcapsules enclosing IPBC (3-iodo-2-propynyl N-butylcarbamate) as active biocidal substance.

| Substances used | Amounts, g |
|---|---|
| Water | 338.4 |
| Gum arabic | 0.6 |
| Silicone defoamer (Aspumit AP, Thor GmbH) | 3.0 |
| IPBC, 50% aqueous dispersion (Acticide IPW 50, Thor GmbH) | 132.0 |
| Citric acid, 12% | 60.0 |
| Formaldehyde-melamine resin (Quecodur DMQ, Thor GmbH) | 66.0 |
| | 600.0 |

For the preparation of the microcapsules the water was introduced first. Polyacrylate, gum arabic, silicone defoamer and IPBC dispersion were stirred into the water. Subsequently the mixture was adjusted with the citric acid to a pH of 1 to 2 and heated to a temperature of 55 to 60° C. Then the formaldehyde-melamine resin was added dropwise over 1 h. Subsequently the mixture was stirred at 55 to 60° C. for 2 h.

The mixture obtained comprised the desired microcapsules and was used unchanged in preparing the microcapsule plaster.

PREPARATION EXAMPLE 4

A silicate-bound white exterior plaster with a grain size of 1.5 to 2 mm was prepared. Prepared first of all was a premix, which was then processed further to form a final mix, i.e., the plaster.

a) Premix

The following substances are mixed for 15 minutes in order to achieve integration or dissolution.

| | % by weight |
|---|---|
| Water | 9.3 |
| Dispersant (Sapetin D 20) | 0.1 |
| Silicate stabilizer (Betolin Quart 20) | 0.3 |
| Rheological additive (Rhodopol 50 MD) | 0.1 |
| Titanium dioxide (Bayertitan R-KB-5) | 3.0 |
| Defoamer (TEGO-Foamex KS 10) | 0.2 |

The following substances are added with stirring to the mixture obtained:

|  | % by weight |
| --- | --- |
| Styrene-acrylate copolymer dispersion, 50% by weight (Mowilith SDM 765 A) | 6.0 |
| Al Mg silicate, D 50 300 μm (Plastorit 05) | 2.5 |
| Reinforcing fiber filler (Arbocel B 400) | 0.5 |
| Calcium carbonate, D 50 5 μm (Omyacarb 5-GU) | 4.0 |
| Calcium carbonate, D 50 7 μm (Omyacarb 10-GU) | 5.0 |
| Calcium carbonate, D 50 23 μm (Omyacarb 40-GU) | 10.0 |

The following substances were added in succession with stirring to the mixture obtained:

|  | % by weight |
| --- | --- |
| Hydrophobicizer (TEGO Phobe 1040) | 0.5 |
| Additive to prevent surface cracking (Lubranil A 1520) | 0.5 |
| Stabilized potassium silicate (waterglass, Betolin P 35, 29% by weight) | 10.0 | b) Final Mix

The premix indicated above under a) was aged for 3 days. Then the following substances were mixed in with slow stirring:

|  | % by weight |
| --- | --- |
| Calcium carbonate, D 50, 160 μm (Omyacarb 130-GU) | 11.0 |
| Calcium carbonate grains, D 50 1200 μm (Austro-tec 10/15) | 37.0 |

The total amount of the quantities indicated above for the premix and the final mix makes 100.0% by weight.

The finished final mix was the exterior plaster. The biocides were then each mixed into this plaster in accordance with the examples below.

PREPARATION EXAMPLE 5

A synthetic-resin-bound white float plaster was prepared in conventional manner from the following substances.

|  | % by weight |
| --- | --- |
| Polyacrylate (Acronal 290 D, BASF AG) | 13.2 |
| Sodium polyphosphate, 25% strength solution | 0.8 |
| Preservative (Acticide MBS, Thor GmbH) | 0.3 |
| Defoamer (Agitan 280) | 0.3 |
| Thickener, polyacrylate, 8% strength ammoniacal solution (Latekoll D, BASF AG) | 0.8 |
| White spirit | 1.0 |

-continued

|  | % by weight |
| --- | --- |
| (180-210° C.) |  |
| Butyl diglycol | 1.0 |
| Basophob WDS (BASF AG) | 0.6 |
| Titanium dioxide, rutile (Kronos 2044, Kronos Titan GmbH) | 2.8 |
| Calcium carbonate (Omyacarb 40-GU) | 39.5 |
| Calcium carbonate (Omyacarb 130-GU) | 25.5 |
| Al Mg silicate (Plastorit 05) | 6.5 |
| Quartz shingle | 4.5 |
| Water | 3.2 |
|  | 100.0 |

The float plaster obtained had a pH of from 8.5 to 9.

INVENTIVE EXAMPLE 1 AND COMPARATIVE EXAMPLE 1

The microcapsule-containing mixture of Preparation Example 1 was added to the synthetic-resin-bound plaster obtained in Preparation Example 5, which has a pH of 8.5. The amount of biocide in the plaster was 578 ppm.

The plaster biocidally treated in this way was used to produce test specimens in the form of plaster disks for the water storage tests. For this purpose the plaster was coated into a circular plastic mold having a diameter of about 5 cm and a depth of 3 mm. The coat thickness corresponded to the grain size of the plaster. The plaster sample was then dried and fully cured. Thereafter the test specimen was removed from the mold and conditioned for the water storage test.

For comparison, plaster disks which differ from the above samples only in that the zinc pyrithione had been mixed into the plaster not in microencapsulated form but instead in normal powder form were produced.

For each sample, the amount of zinc pyrithione in the plaster before and after water storage for various periods of time was measured.

The samples were subjected to static water storage in 1 l of DIBT solution, the solution being replaced completely every 24 h with the exception of the 7th day.

The DIBT solution is an alkaline solution specified by the Deutsches Institut für Bautechnik (DIBT) [German Institute of Construction Engineering] for the water storage of samples. The solution has a pH of 12.5 and is composed of the following substances:

| Sodium hydroxide | 0.88 g |
| --- | --- |
| Potassium hydroxide | 3.45 g |
| Calcium hydroxide | 0.48 g |
| Water | remainder to 1 l |

The results are reported below.

| | Residual biocide in plaster (pH 8.5), ppm | | | |
|---|---|---|---|---|
| | Storage in DIBT solution, days | | | |
| | None | 2 | 5 | 10 |
| Inventive Example 1 | 578 | 478 | 259 | 187 |
| Comparative Example 1 | 560 | 21 | 4 | 0 |

INVENTIVE EXAMPLE 2 AND COMPARATIVE EXAMPLE 2

Inventive Example 1 and Comparative Example 1 were repeated but with the modification that now the silicate-bound float plaster of Preparation Example 5, with a pH of 11.5, was used and storage in water took place for 1, 2 and 7 days.

The results are reported below.

| | Residual biocide in plaster (pH 11.5), ppm | | | |
|---|---|---|---|---|
| | Storage in water, days | | | |
| | None | 2 | 5 | 10 |
| Inventive Example 2 | 531 | 423 | 325 | 21 |
| Comparative Example 2 | 568 | 2 | 0 | 0 |

INVENTIVE EXAMPLE 3 AND COMPARATIVE EXAMPLE 3

Inventive Example 1 and Comparative Example 1 were essentially repeated, but with certain modifications. These were to the effect that, instead of the zinc pyrithione microcapsules obtained in accordance with Preparation Example 1, the microcapsules containing DCOIT as active biocidal substance, obtained in accordance with Preparation Example 2, were now used, and instead of water storage the samples were heated at a temperature of 54° C. for 4 weeks. The silicate-bound plaster of Preparation Example 4 was used, with a pH of 11.5.

The results are reported below.

| | Residual biocide in plaster (pH 11.5), and biocide degradation after heat treatment at 54° C. | | |
|---|---|---|---|
| | Heat treatment, ppm | | |
| | None | 4 weeks | Degradation, % |
| Inventive Example 3 | 508 | 474 | 6.7 |
| Comparative Example 3 | 521 | 382 | 26.7 |

INVENTIVE EXAMPLE 4 AND COMPARATIVE EXAMPLE 4

Inventive Example 3 and Comparative Example 3 were repeated, but with the modification that instead of the microcapsules of Preparation Example 2, containing DCOIT, the microcapsules of Preparation Example 3, containing IPBC, were now used.

The results are reported below.

| | Residual biocide in plaster (pH 11.5), and biocide degradation after heat treatment at 54° C. | | |
|---|---|---|---|
| | Heat treatment, ppm | | |
| | None | 4 weeks | Degradation, % |
| Inventive Example 4 | 280 | 256 | 8.6 |
| Comparative Example 4 | 291 | 211 | 27.5 |

INVENTIVE EXAMPLES 5 AND 6 AND COMPARATIVE EXAMPLES 5, 6 and 7

Fungal growth on the sample surface was investigated.

The silicate-bound plaster of Preparation Example 4, applied to a support plate, was either biocide-free (Comparative Example 5) or was admixed with 100 ppm of zinc pyrithione (Comparative Example 6), 200 ppm of zinc pyrithione (Comparative Example 7), 100 ppm of microencapsulated zinc pyrithione (Inventive Example 5) or 200 ppm of microencapsulated zinc pyrithione (Inventive Example 6).

The plaster samples were applied as a coat to calcium silicate plates which measured 4.5 cm×9 cm and have undergone water storage beforehand. The coat thickness of the plaster was within the order of magnitude of its grain size, i.e., from 1.5 to 2 mm.

After the samples had cured, they were subjected to water storage as in Inventive Example 1.

The test for fungal growth took place as follows:

The plaster samples were poured into a conventional agar nutrient medium. Thereafter the samples were sprayed with a fungal spore suspension. The suspension contained equal proportions of the following test organisms:

*Alternaria alternata*
*Aspergillus niger*
*Cladosporium cladosporoides*
*Penicillium funiculosum*
*Ulocladium atrum*

The total concentration of the fungal inoculum was $10^6$ spores/ml.

The samples were stored in the usual way over a relatively long period of time under growth conditions optimum for fungi. Thereafter the fungal growth on the sample surface was evaluated.

The fungal growth on the sample surface was evaluated using the following scale:

| Growth rate | Fungal growth |
|---|---|
| 0 | No growth visible |
| x | Minimal growth (up to 25% surface coverage) |
| xx | Slight growth (up to 50% surface coverage) |
| xxx | Moderate growth (up to 75% surface coverage) |
| xxxx | Severe growth (up to 100% surface coverage) |

The results of the fungal growth test for the samples investigated are reported below.

| | Fungal growth on the surface of the plaster (pH 11–12) without/with zinc pyrithione | | | |
|---|---|---|---|---|
| | Zinc pyrithione | Water storage | | |
| | ppm | None | 2 days | 5 days |
| Comparative Example 5 | 0 | xxx | xxxx | xxx |
| Comparative Example 6 | 100 | x | x | xxx |
| Comparative Example 7 | 200 | 0 | x | xx |
| Inventive Example 5 | 100 (encapsulated) | 0 | 0 | 0 |
| Inventive Example 6 | 200 (encapsulated) | 0 | 0 | 0 |

The invention claimd is:

1. A coating material for protection against microorganism infestation on surfaces exposed to the effects of damp or water; said coating material having a pH of at least 11.0 comprising a biocide which is bound in a carrier material composed of particulate solids of a wall material containing a formaldehyde-melamine resin which protects the biocide from being decomposed in a strongly alkaline environment having a pH of at least 11.0 which is released retardedly therefrom and wherein the biocide is a zinc pyrithione, 4,5-dichloro-2-octylisothiazolin-3-one, 3-iodo-2-propynyl N-butylcarbamate, 2-n-octylisothiazolin-3-one, methyl 1H-benzimidazol-2-ylcarbamate, or $N^2$-t-butyl-$N^4$-ethyl-6-methylthio-1,3,5-triazine-2,4-iyldiamine or a mixture of two or more of these compounds.

2. The coating material of claim 1, characterized in that the coating is a silicate-bound or mineral plaster having a pH of at least 11.

3. The coating material of claim 1, characterized in that the coating prior to application is a synthetic-resin-bound or silicone-resin-bound plaster having a pH of below 11, wherein said plaster is applied to a strongly alkaline substrate, whereafter alkaline compounds gradually penetrate from the substrate material into the coating containing the biocide bound in the carrier material.

4. The coating material of claim 1, characterized in that the coating is a silicate-bound paint having a pH of at least 11.

5. The coating material of claim 1, characterized in that the coating is a synthetic-resin-bound or silicone-resin-bound paint having a pH of below 11.

6. The coating material of one of claim 1, characterized in that the particulate solids of the carrier material are granular particles having cavities.

7. The coating material of claim 6, characterized in that the granular particles having cavities are microcapsules.

8. The coating material of claim 7, characterized in that the wall material of the microcapsules is composed primarily of a formaldehyde-melamine resin.

9. The coating material of claim 6, characterized in that the granular particles with cavities are composed of a foamed ceramic material or a zeolite.

* * * * *